Figure 2:
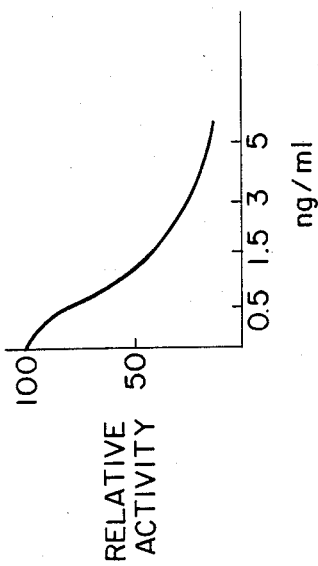

United States Patent [19]

Kasahara et al.

[11] Patent Number: 4,649,105
[45] Date of Patent: * Mar. 10, 1987

[54] METHOD OF MEASURING BIOLOGICAL LIGAND

[75] Inventors: Yasushi Kasahara; Yoshihiro Ashihara; Hiromasa Suzuki, all of Tokyo, Japan

[73] Assignee: Fujirebio Kabushiki Kaisha, Tokyo, Japan

[*] Notice: The portion of the term of this patent subsequent to Apr. 15, 2003 has been disclaimed.

[21] Appl. No.: 603,499

[22] Filed: Apr. 24, 1984

[30] Foreign Application Priority Data

Apr. 30, 1983 [JP] Japan ................................. 58-77255

[51] Int. Cl.$^4$ ................. G01N 33/543; G01N 33/545; G01N 33/569; G01N 33/574
[52] U.S. Cl. .......................................... 435/5; 435/7; 435/15; 435/188; 436/518; 436/531; 436/813; 436/817
[58] Field of Search ............... 436/501, 518, 531, 537; 435/7

[56] References Cited

U.S. PATENT DOCUMENTS 4,208,479  6/1980  Zuk et al. ............................. 436/537

Primary Examiner—Sidney Marantz
Assistant Examiner—David A. Saunders
Attorney, Agent, or Firm—Burgess, Ryan & Wayne

[57] ABSTRACT

A method of measuring a biological ligand comprises allowing to coexist a biologically active composition comprising an immobilization phase of a particular antibody or a particular ligand and an immobilization phase of a biotinyl enzyme or a biotinyl enzyme inhibitor, a water-soluble conjugate of the ligand or the antibody and the biotinyl enzyme inhibitor or the biotinyl enzyme, and the ligand to be measured in an aqueous solution, and measuring the remaining biotinyl enzyme activity or the biotinyl enzyme inhibitory activity. This method is highly sensitive and specific, and it is suitable as a clinical test for the determination of physiological substances and trace components in humoral fluid.

14 Claims, 4 Drawing Figures

METHOD OF MEASURING BIOLOGICAL LIGAND

This invention relates to a method of measuring a biological ligand, for example, medicinal substances and trace components derived from various diseases in a humoral fluid such as blood, by using a biologically active composition where two kinds of biologically active substances are separately immbolized.

The measurement of the concentration of a drug administered to a patient such as digoxin and theophylline, in the blood is important in the appropriate treatment, and the detection of the trace components derived from various diseases such as cancer in the blood of an examinee is important in early diagnoses of the diseases.

Accordingly, various methods to detect these trace components in blood have been developed, and among them, enzyme immunoassay is widely employed because of its superiorities in sensitivity, in specificity and in rapid treatment of a large number of samples. However, in the case of the conventional enzyme immunoassay, the sensitivity is not sufficient, and it is not easy to obtain an exact concentration because of its complicated washing procedures and transferring of tubes.

The inventors have investigated a novel enzyme immunoassay where a biologically active composition comprising an immobilization phase of an antigen or an antibody and an immobilization phase of an enzyme or an enzyme inhibitor or activator is employed (U.S. patent appln. Ser. No. 491,661).

In the present invention, biotin-avidin reaction is introduced into this method, and the method is characterized by higher sensitivity and simplicity by utilizing their small coupling constant. Thus, the method of the invention is characterized by using a biologically active composition comprising an immobilization phase of an antibody capable of reacting with the ligand (1) to be measured or a ligand (2) capable of reacting with the above antibody and an immobilization phase of a biotinyl enzyme or a biotinyl enzyme inhibitor and a conjugate of the above ligand (2) or the above antibody and a biotinyl enzyme inhibitor capable of reacting with the above biotinyl enzyme or a biotinyl enzyme capable of reacting with the above biotinyl enzyme inhibitor.

The subject to be measured by the method of the invention is a ligand (1). The ligand (1) is a substance having one or more antigenic determinants, and includes, for example, hormones derived from various endocrine glands; plasma proteins such as immunoglobulin, albumin and ferritin; viral antigens such as HB antigen, bacteria, α-fetoprotein, and carcinoembryonic antigens. This ligand (1) also includes a hapten and a first antibody in the double antibody method. The ligand (1) includes, for example, the conjugate of the desired antigen to be measured and a first antibody in the case of the double antibody method.

The biologically active composition comprises the immobilization phase of the antibody or the ligand (2) and the immobilization phase of the biotinyl enzyme or the biotinyl enzyme inhibitor.

The antibody reacts with the ligand (1), and the ligand (2) reacts with this antibody. At least one antigenic determinant should be common to these ligands and the antibody should be the antibody against this common antigenic determinant. The antibody includes fragments of immunoglobulin such as F(ab')$_2$, Fab' and Fab. All antigenic determinants of the ligand (2) may be equal to those of the ligand (1), and accordingly, the ligand (2) may be identical with the ligand (1).

Such an antibody may be produced according to known methods of producing an antibody. For example, the ligand (1), the ligand (2) or a conjugate of either of these ligands and a protein material is injected once or several times into the subcutaneous region of the back, foot pad or femoral muscle of a warm-blooded animal such as a rabbit, goat, horse, guinea pig and chicken, in an amount of about 0.3 to 2 mg per kg together with an adjuvant, thereby producing the antibody in the humoral fluid such as serum. This humoral fluid, as it is, may be used as the antibody, and however, the antibody may preferably be separated according to a conventional isolation method of an immunoglobulin.

On the other hand, the antibody may be produced as a monoclonal antibody. In this case, one of the above antigens is injected several times into the abdominal cavity of a mouse together with an adjuvant, and its spleen is excised. The spleen cell is fused with a mouse myeloma cell by a conventional method involving the use of polyethylene glycol. The hybridoma thus obtained is cultured and cloned, and the cell capable of producing the desired antibody is obtained. This cell is injected into the abdominal cavity of a mouse, and multiplied. Then, ascites are collected, and the desired antibody is separated from the ascites.

The biotinyl enzyme has a biotinyl group in its active site and includes, for example, propionyl CoA carboxylase, acetyl CoA carboxylase, pyruvate carboxylase, methylmalonyl CoA carboxylase, methylmalonyl CoA transcarboxylase, methylcrotonyl CoA carboxylase.

The biotinyl enzyme inhibitor includes, for example, avidin, streptoavidin and their derivatives capable of binding to biotin. Such derivatives are, for example, modified ones with general chemical modifiers such as acetylated ones. The coupling constants of the derivatives are preferably small.

Since the ligand (2) or the antibody and the biotinyl enzyme or the biotinyl enzyme inhibitor are immobilized in the biologically active composition, there are four kinds of the combinations which are the ligand (2) and the biotinyl enzyme, the ligand (2) and the biotinyl enzyme inhibitor, the antibody and the biotinyl enzyme, and the antibody and the biotinyl enzyme inhibitor.

Such a biologically active composition is characterized by the separation of the immobilization phase of the ligand (2) or the antibody from the immobilization phase of the biotinyl enzyme or the biotinyl enzyme inhibitor. This phase separation means that when the conjugate of a ligand (2) or an antibody and a biotinyl enzyme or a biotinyl enzyme inhibitor described later reacts and combines with one immobilization phase, this conjugate cannot combine with the other immobilization phase. However, of course, the conjugate may react with both immobilization phases at the boundary region.

Specifically, such a biologically active composition includes a polymer material on which a ligand (2) or an antibody and a biotinyl enzyme or a biotinyl enzyme inhibitor are at different parts of the same polymer. It also includes two polymer materials which are attached to each other, and on one of which a ligand (2) or an antibody is immobilized and on the other of which a biotinyl enzyme or a biotinyl enzyme inhibitor is immobilized. In addition, in the case of a considerably large particle, for example, one having a diameter of more than about 3 mm, since the contacting area between the particles is minor in comparison with the total surface area, the above biologically active composition may consist of a mixture of two particle groups. Thus, on the particles belonging to one group, a ligand (2) or an antibody is immobilized, and on the particles belonging to the other group, a biotinyl enzyme or a biotinyl enzyme inhibitor is immobilized. In this case, the particles of one group may be replaced by a tube.

The biologically active composition is prepared as follows. In the case of the polymer material where the biologically active substances are immobilized at different parts of the same polymer, this polymer material may be produced by using a block-copolymer or a graft-copolymer. In this case, a ligand (2) or an antibody and a biotinyl enzyme or a biotinyl enzyme inhibitor are separately immobilized by using the different functional groups of the above copolymer. As the functional groups, —NH$_2$, —COOH, —CHO, —OH and —SH may be used. While, in a case where the biologically active substance such as a kind of a ligand (2) and a kind of a biotinyl enzyme inhibitor does not lose its activity through the copolymerization reaction, its immobilization may be carried out prior to the copolymerization. In such case, the functional groups may be identical.

In the case of the two polymer materials which are attached to each other, the immobilizations may be carried out before or after they are attached to each other. This may be carried out by welding or pasting.

The shape of the composition includes a sphere, a disk, a cube or a tube.

The immobilization may be carried out according to known methods. A protein material among the biologically active substances may be immobilized by using a known method of immobilizing a biologically active protein such as an enzyme. This known method includes the covalently bound method such as the diazotization method, the peptide synthesis method and the alkylation method, the ionic bond method and the physical adsorption method. In the case of other than the protein material, a suitable method is selected by considering the functional group of the biologically active substance and that of the carrier material. The immobilized ligand (2) includes the reaction product of a ligand and a first antibody in the case where the first antibody is allowed to react with the ligand covalently bound to a carrier material and then the reaction product is further allowed to react with the second antibody.

The ratio of the ligand (2) or the antibody to the biotinyl enzyme or the biotinyl enzyme immobilized on the biologically active composition is decided by considering their reactivity, the sensitivity of the measuring apparatus, etc.

The constituents of the conjugate is the antibody capable of reacting with the ligand (1) and the ligand (2) immobilized on the biologically active composition or the ligand (2) capable of reacting with the antibody of the biologically active composition and the biotinyl enzyme inhibitor capable of reacting with the biotinyl enzyme of the biologically active composition or the biotinyl enzyme capable of reacting with the biotinyl enzyme inhibitor of the biologically active composition. Accordingly, there are four couples of the combination which are the ligand (2) and the biotinyl enzyme, the ligand (2) and the biotinyl enzyme inhibitor, the antibody and the biotinyl enzyme, and the antibody and the biotinyl enzyme inhibitor. However, since these constituents should react with the corresponding immobilization phase of the biologically active composition, they are automatically determined according to the kind of the biologically active composition. It is necessary that the conjugate is water-soluble as it is reacted with the biologically active composition.

Where both materials to be combined are protein, such conjugate may be produced according to the known cross-linking method or the peptide synthesis method of immobilizing a biologically active protein such as an enzyme. Where one or both materials are not protein, a suitable method to produce the conjugate is selected by considering the functional groups of the materials to be combined. The molar ratio of the conjugate is not limited to 1:1, and the suitable ratio is determined by considering various measuring conditions.

When the measurement of the ligand (1) is carried out by allowing it to coexist with the biologically active composition, the conjugate and the ligand (1) to be measured in an aqueous solution, the order of the addition is not limited. It is not necessary to maintain coexistence throughout the reaction; it may be temporary. For example, where the measurement includes the ligand (1) to be measured and the conjugate of a ligand (2) and a biotinyl enzyme is allowed to react with an antibody immobilized on a tube, then the remaining conjugate is scavenged by adding a biotinyl enzyme inhibitor immobilized on a bead.

The aqueous solution may preferably be kept at a suitable pH for the reaction of the ligands and the antibody and for the reaction of the biotinyl enzyme and the biotinyl enzyme inhibitor. For this purpose, a buffer solution such as a phosphate buffer solution, a borate buffer solution and a tris buffer solution is preferably used. The suitable pH depends on the kinds of the ligands, the antibody, the biotinyl enzyme and the biotinyl enzyme inhibitor. It is usually in the range of a pH of about 5 to 8. The suitable temperature of the aqueous solution is also different according to the kinds of the ligands, the antibody, the biotinyl enzyme and the biotinyl enzyme inhibitor; it is usually at about 15° to 45° C.

After the reaction, the biotinyl enzyme activity or the biotinyl enzyme activity of the biologically active composition or the aqueous solution is measured. The measurement is carried out according to a known method. For example, in the case of propionyl CoA carboxylase, ADP produced during the reaction is allowed to react in the presence of pyruvate kinase and lactate dehydrogenase, and the decrease of NADH is calorimetrically determined. In the case of methylmalonyl CoA transcarboxylase, oxalacetic acid produced is coverted to malic acid in the presence of malate dehydrogenase, and the decrease of NADH is measured. Where propionyl CoA carboxylase is used, ATP produced by a reverse reaction is allowed to react in the presence of luciferase and luciferin, and thereby bioluminescence radiates. When this bioluminescence is measured by using a photon counter, the ATP concentration lower than $10^{-15}$M can be determined. This method is suitable for determining an extremely small amount of the ligand (1).

According to the method of the invention, a ligand (1) is determined in a high sensitivity. For example, in the case of using a biotinyl enzyme and avidin, a ligand (1) in an amount of $10^{-11}$ gram can be determined. Furthermore, the operation of the present method is a simple one. For example, the separation process of a bound and a free material is not necessary, and a ligand (1) can easily and inexpensively be determined.

EXAMPLE 1

(1) Preparation of Conjugate 5 mg of avidin was dissolved in 1 ml of 0.1M phosphate buffer solution of pH 6.3, and 100 μl of 2 mg/ml 4-maleimidomethyl cyclohexane-1-carboxylic acid succimide ester (CHMS) dioxane solution was added, and allowed to react at room temperature for one hour. The reaction solution was introduced into a column of SEPHADEX G-25 an anion exchange resin containing quaternary ammonium groups, (0.1M phosphate buffer solution—1 mM EDTA pH 6.5), and gel filtration was carried out. The protein fractions were collected as CHMS induced avidin fractions.

Goat anti-human α-fetoprotein (AFP) antibody was purified by using an AFP affinity column, and 10 mgs of the purified IgG was dissolved in 1.0 ml of 0.1M phosphate buffer solution—1 mM EDTA pH 6.0. 0.1 ml of a 0.1M 2-mercaptoethylamine solution was added to this solution, and the resulting solution was allowed to react at 37° C. for 90 minutes. The reaction solution was passed through a column of SEPHADEX G-25, and the void fractions were collected. The above CHMS induced avidin was added to the void fractions, and the pH of the mixture was adjusted to 6.8. The mixture was allowed to react at 4° C. for 24 hours, and the reaction solution was concentrated by using PEG-20,000. The concentrate was separated by gel filtration using SEPHACRYL S-300 an anion exchange resin, and about 7 mg of the conjugate of anti-AFP IgG-avidin was obtained.

(2) Preparation of Biologically Active Composition

A spherical nylon bead 4 mm in diameter was treated with 3N HCl for 24 hours to liberate its amino group. The treated nylon bead was washed with water, and immersed in a 0.1M phosphate buffer solution—5 mM EDTA pH 7.5. 10 mg/ml of S-acetylmercaptosuccinic anhydride dimethyl sulfoxide solution in a volume of one tenth of the above buffer solution was added, and allowed to react at 37° C. for 3 hours. 1M hydroxylamine solution (ph 7.5) in a volume of one tenth of the above reaction solution was added to the solution, and allowed to react at 37° C. for 1 hour. Then, the nylon bead was washed with the above buffer solution.

5 mg of CHMS induced propionyl CoA carboxylase prepared in the same manner as the case of avidin of item (i) was dissolved in a 0.1M phosphate buffer solution—1 mM EDTA (ph 6.0), and this solution was added to the washed nylon bead. The solution was adjusted to pH 7.0, and allowed to react at 4° C. overnight. Then, the nylon bead was washed with the above buffer solution at a pH of 7.5, and preserved in the above buffer solution containing 1% BSA to obtain the immobilized propionyl CoA carboxylase bead.

A spherical polystyrene bead 3.2 mm in diameter was washed with water, immersed overnight in a phosphate buffer solution of a pH of 7.5 containing AFP ($OD_{280}=0.1$) at 4° C., whereby AFP was adsorbed on the polystyrene bead. This polystyrene bead was washed sufficiently with a phosphate buffer solution of pH 7.5, and preserved in the above buffer solution containing 1% BSA to obtain the immobilized AFP bead.

(3) Measurement of AFP

Each one piece of the immobilized propionyl CoA carboxylase bead and the immobilized AFP bead were placed in a test tube, and 800 μl of 50 mM tris buffer solution—0.14M NaCl—0.2% BSA (pH 7.8) was added.

800 ng/ml AFP solution was prepared, and the solution was diluted to produce 4n diluted solution series.

Each 100 μl of the diluted solution and then 100 of the AFP IgG—avidin conjugate of item (1) were added to each test tube, and allowed to stand at room temperature for one hour.

Subsequently, each 1 ml of an enzyme substrate solution (containing 0.1M KCl—50 mM $KHCO_3$—4 mM $MgCl_2$—2 mM reduced glutathione—2 mM ATP—1 mM phosphoenolpyruvic acid—2,500 U/l pyruvate kinase—3,500 U/l lactate dehydrogenase—0.15 mM NADH—2 mM propionyl CoA) was added to each test tube, and the absorbance at 340 nm of the reaction solution at 37° C. was measured to determine the relation between the AFP concentration and the activity of propionyl CoA carboxylase.

Figure 1:
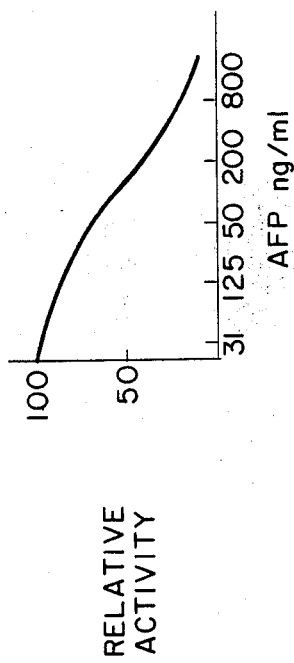

The result is shown in FIG. 1.

Next, AFP concentrations of various human sera were measured. Each serum was allowed to react with immobilized avidin glass beads for 30 minutes, and the supernatant was diluted 10 times. Using each 100 μl of the diluted supernatant, the measurements were carried out in the same manner as above. The AFP concentrations of each serum were determined by using the curve of FIG. 1 as the calibration curve. On the other hand, the AFP concentrations of the same sera were measured by the conventional radioimmunoassay (RIA). The results are shown in the following table.

| Serum | AFP Concentration (mg/ml) | |
|---|---|---|
| | The method of the invention | RIA method |
| A1 | 15.8 | 17.5 |
| A2 | 450 | 432 |
| A3 | 142 | 158 |
| A4 | 6.3 | 6.9 |
| A5 | 748 | 780 |
| A6 | 210 | 200 |

EXAMPLE 2

(1) Preparation of Conjugate 5 mg of pyruvate carboxylase was dissolved in 1 ml of 0.1M phosphate buffer solution of a pH of 6.3, and 100 of 2 mg/ml CHMS dioxane solution was added. The mixture was allowed to react at room temperature for 90 minutes. The reaction solution was then separated by gel filtration using a column of SEPHADEX G-25 which was previously equilibrated with a 0.1M phosphate buffer solution—1 mM EDTA (pH 6.5) and the void fractions were collected. The fractions were concentrated to 1 ml by using PEG 20,000 to obtain CHM induced pyruvate carboxylase.

5 mg of anti-digoxin rabbit IgG was dissolved in 0.1M phosphate buffer solution—5 mM EDTA of a pH of 7.5, and 100 μl of 9 mg/ml acetylmercaptosuccinic anhydride dimethyl sulfoxide solution was added. The mixture was allowed to react at 37° C. for one hour. 110 μl of 1M hydroxylamine solution was added to the reaction mixture, and allowed to react at 37° C. for 30 minutes. The reaction solution was then treated by gel filtration using a SEPHADEX G-25 column as above, and the void fractions were collected. The above CHM induced pyruvate carboxylase was added to the void fractions, and allowed to stand at 4° C. overnight. The reaction solution was separated by gel filtration using SEPHACRYL S-300, and the fractions of the conjugate of anti-digoxin IgG—pyruvate carboxylase of a molar ratio of 1:1 were collected.

(2) Preparation of Biologically Active Composition 2 ml of 100 μg/ml avidin—20 mM PBS pH 7.8 solution was added to a polystyrene tube (8 mm×50 cm), and allowed to stand at 4° C. for 16 hours. This tube was washed 4 times with a saline solution. 5% BSA aqueous solution was added to this tube, and allowed to stand at room temperature for 3 hours to obtain an avidin-sensitized tube.

Next, digoxin was oxidized by $NaIO_4$, and allowed to combine with BSA. 20 mg of the BSA—digoxin combination material was dissolved in 100 ml of 0.02M phosphate buffer solution at a pH of 8.0, and 60 pieces of polystyrene beads of a diameter of 4 mm were added. This mixture was allowed to stand at 4° C. for 16 hours to obtain digoxin-sensitized polystyrene beads.

(3) Measurement of Digoxin

Each one piece of the digoxin-sensitized bead was added to the avidin-sensitized tube, and 400 μl of 20 mM tris buffer solution—0.14M NaCl—0.2% BSA (pH 8.0) was added to them. Each 100 μl of a diluted digoxin solution) 0-5 ng/ml) and 100 μl of the conjugate of anti-digoxin IgG—pyruvate carboxylase prepared in item (1) were added to the mixture, and allowed to stand at 30° C. for 1 hour.

Subsequently, each 1 ml of an enzyme substrate solution (containing 0.1M KCl—50 mM $KHCO_3$—4 mM $MgCl_2$—2 mM ATP—2 mM reduced glutathione—4 mM pyruvic acid—0.23 mM NADH—3000 U/l malate dehydrogenase, pH 7.5) was added to this tube, and the decreasing rate of the absorbance at 340 nm at 37° C. was measured. The relation between the relative activity of pyruvate carboxylase and the concentration of digoxin thus obtained is plotted in FIG. 2.

Next, digoxin concentrations of various human sera were measured. Each serum was allowed to react with immobilized avidin glass beads for 30 minutes, and the supernatant was diluted 10 times. Using each 100 μl of the diluted supernatant, the measurements were carried out in the same manner as above. The results are shown in the following table.

| Serum | Digoxin Concentration (ng/ml) | |
| --- | --- | --- |
| | The method of the invention | RIA method |
| B1 | 1.5 | 1.3 |
| B2 | 2.2 | 2.6 |
| B3 | 4.1 | 4.0 |
| B4 | 0.8 | 1.1 |
| B5 | 1.1 | 1.3 |

EXAMPLE 3

(1) Preparation of Conjugate 5 mg of anti-ferritin goat IgG was dissolved in 1 ml of 0.1M phosphate buffer solution—1 mM EDTA of a pH of 6.3, and 100 μl of 2 mg/ml CHMS dioxane solution was added to this. The mixture was allowed to react at room temperature for 90 minutes. The reaction mixture was separated by gel filtration using SEPHADEX G-25, and the void fractions were collected.

5 mg of ferritin and 1 mg of avidin were dissolved in 1 ml of 0.1M phosphate buffer solution of a pH of 6.8, and 100 μl of 1% glutaraldehyde aqueous solution was added to this, and allowed to react at 30° C. for 3 hours. The reaction mixture was separated by gel filtration using SEPHACRYL S-300, and the fractions of the combination of ferritin and avidin of a molar ratio of 1:1 were collected. The fractions were lyophilized to obtain 3 mg of the desired conjugate of ferritin-avidin.

(2) Preparation of Biologically Active Composition

A carrier plate was prepared from polystyrene plate by the known polymer blend method as follows:

Each 10 mg of poly-L-cysteine and poly-L-lysine was dissolved in a dimethyl sulfoxide—ether mixture solvent, and applied on the above plate. The solvent was then evaporated under reduced pressure. A micro phase separation between the poly-L-cysteine layer and the poly-L-lysine layer formed on the surface of the plate owing to the difference in their condensation energies. The SH group content of the plate was measured by the dithiopyridone method and the amino group content was measured by the ninhydrin method; the ratio of the SH groups to amino groups was found to be about 1:1. This polystyrene plate was cut into a square of 0.8 cm, and used as a carrier plate.

This carrier plate was immersed in acetyl CoA carboxylase aqueous solution, and water-soluble carbodiimide was added until its concentration was 100 mg/10 ml. The mixture was adjusted to a pH of 5.5 by using 0.1N NaOH, and allowed to stand at 4° C. for 16 hours. Then, the plate was sufficiently washed with a 20 mM phosphate buffered saline solution of a pH of 7.0.

This plate was immersed in 0.1M phosphate buffer solution—1 mM EDTA of a pH of 6.5, and the CHM induced anti-ferritin goat IgG prepared in item (1) was added in a concentration of 2 mg/ml. The mixture was allowed to react at 30° C. for 2 hours, and the plate was sufficiently washed with 20 mM PBS at a pH of 7.0 to obtain the biologically active composition.

(3) Measurement of Ferritin

Figure 3:
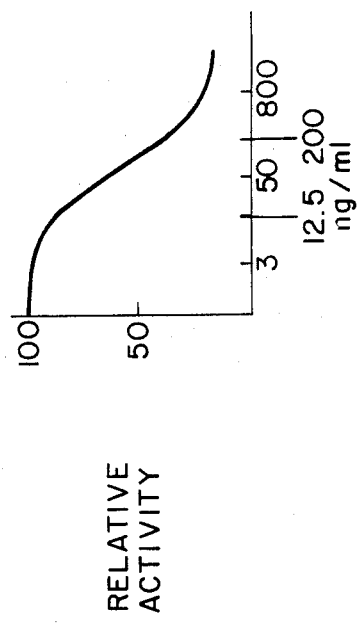

Each one piece of the biologically active composition prepared in item (2) was placed in a glass test tube, and 400 μl of 20 mM of a tris buffer solution—0.14M NaCl—0.2% BSA at a pH of 8.0 was added. 50 μl of a ferritin solution diluted in various concentrations and 50 μl of the solution of the conjugate prepared in item (1) were added to the test tube, and allowed to incubate at 30° C. for 1 hour. 1 ml of a substrate solution (containing 0.1M KCl—$10^{-3}$M acetyl CoA—0.3M $KHCO_3$—3 mM ATP—0.23 mM NADH 0.2 mM reduced glutathione—1.5 mM phosphoenolpyruvic acid—2,500 U/l pyruvate kinase—3,500 U/l lactate dehydrogenase, at a pH of 7.8) was added to each test tube, and the decreasing rate of the absorbance at 340 nm at 37° C. was measured. The relation between the relative activity of acetyl CoA carboxylase and the concentration of ferritin thus obtained is plotted in FIG. 3.

Next, ferritin concentrations of various human sera were measured. Each serum was allowed to react with immobilized avidin glass beads for 30 minutes, and the supernatant was diluted 10 times. Using each 100 μl of the diluted supernatant, the measurements were carried out in the same manner as above. The results are shown in the following table. For the purpose of comparison, the ferritin concentrations of the same sera were measured by the conventional enzyme immunoassay (EIA) method. The results are also shown in the same table.

| | Ferritin Concentrations (ng/ml) | |
|---|---|---|
| Serum | The method of the invention | EIA method |
| C1 | 19 | 21 |
| C2 | 169 | 176 |
| C3 | 145 | 146 |
| C4 | 38 | 33 |
| C5 | 395 | 400 |

EXAMPLE 4

(1) Preparation of Combination Material 5 mg of ferritin and 10 mg of propionyl CoA carboxylase were dissolved in 1 ml of 0.1M phosphate buffer solution of a pH of 6.8, and 100 μl of 1% glutaraldehyde aqueous solution was added thereto. The mixture was allowed to react at 30° C. for 4 hours. The reaction mixture was separated by gel filtration using 20 mM phosphate buffered (pH 7.0) Sepharose 4B, and the fractions of the conjugate of a molar ratio of 1:1 were collected.

(2) Preparation of Biologically Active Composition

A biologically active composition where antiferritin goat IgG and avidin were separately immobilized was prepared by using the carrier plate prepared in item (2) of Example 3 and according to the method of item (2) of Example 3.

(3) Measurement of Ferritin

Each one piece of the biologically active composition prepared in item (2) was placed in a test tube, and 800 μl of 50 mM tris buffer solution—0.14M NaCl—0.2% BSA (pH 7.8) was added. A ferritin solution of 1,000 ng/ml was diluted, and a 4n diluted solution series was prepared. Each 100 μl of the diluted solution and 100 μl of the conjugate prepared in item (1) were added to the test tube, and allowed to stand at room temperature for 1 hour.

Figure 4:
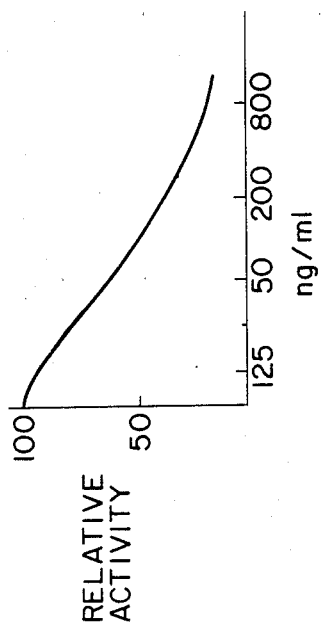

Each 1 ml of the same enzyme substrate solution as employed in Example 1 was added to each test tube, and the decreasing rate of the absorbance at 340 nm at 37° C. was measured to determine the relation between the ferritin concentration and the relative activity of propionyl CoA carboxylase. The result is shown in FIG. 4.

Next, ferritin concentrations of various human sera were measured. Each serum was allowed to react with immobilized avidin glass beads for 30 minutes, and the supernatant was diluted 10 times. Using each 100 μl of the diluted supernatant, the measurements were carried out in the same manner as above. The results are shown in the following table. For the purpose of comparison, the ferritin concentrations of the same sera were measured by the conventional EIA method. The results are also shown in the same table.

| | Ferritin Concentration (ng/ml) | |
|---|---|---|
| Serum | The method of the invention | EIA method |
| D1 | 20 | 21 |
| D2 | 180 | 176 |
| D3 | 150 | 146 |
| D4 | 35 | 33 |
| D5 | 391 | 400 |

What is claimed is:

1. A method of measuring a biological ligand which comprises the steps of:
   (a) forming a biologically active composition by:
      (i) immobilizing on a first solid phase an antibody or an antibody fragment capable of reacting with the ligand (1) to be measured;
      (ii) immobilizing on a second solid phase a biotinyl enzyme;
   (b) contacting said biologically active composition with:
      (1) an aqueous solution of a biological ligand (2) capable of reacting with said antibody or said antibody fragment, said biological ligand (2) being conjugated to a biotinyl enzyme inhibitor capable of reacting with said biotinyl enzyme;
      (2) the ligand (1) to be measured; and
   (c) measuring the biotinyl enzyme activity of said biologically active composition or the biotinyl enzyme inhibitory activity of said aqueous solution.

2. A method of measuring a biological ligand which comprises the steps of:
   (a) forming a biologically active composition by:
      (i) immobilizing on a first solid phase an antibody or an antibody fragment capable of reacting with the ligand (1) to be measured;
      (ii) immobilizing on a second solid phase a biotinyl enzyme inhibitor;
   (b) contacting said biologically active composition with:
      (1) an aqueous solution of a biological ligand (2) capable of reacting with said antibody or said antibody fragment, said biological ligand (2) being conjugated to a biotinyl enzyme capable of reacting with said biotinyl enzyme inhibitor;
      (2) the ligand (1) to be measured; and
   (c) measuring the biotinyl enzyme inhibitory activity of said biologically active composition or the biotinyl enzyme activity of said aqueous solution.

3. A method of measuring a biological ligand which comprises the steps of:
   (a) forming a biologically active composition by:
      (i) immobilizing on a first solid phase a biological ligand (2) capable of reacting with an antibody or with an antibody fragment;
      (ii) immobilizing on a second solid phase a biotinyl enzyme;
   (b) contacting said biologically active composition with:
      (1) an aqueous solution of an antibody or of an antibody fragment capable of reacting with said ligand (2), said antibody or said antibody fragment being conjugated to a biotinyl enzyme inhibitor capable of reacting with said biotinyl enzyme;
      (2) the ligand (1) to be measured; and
   (c) measuring the biotinyl enzyme activity of said biologically active composition or the biotinyl inhibitory activity of said aqueous solution.

4. A method of measuring a biological ligand which comprises the steps of:
   (a) forming a biologically active composition by:
      (i) immobilizing on a first solid phase a biological ligand (2) capable of reacting with an antibody or with an antibody fragment;
      (ii) immobilizing on a second solid phase a biotinyl enzyme inhibitor;
   (b) contacting said biologically active composition with:

(1) an aqueous solution of an antibody or of an antibody fragment capable of reaction with said ligand (2), said antibody or said antibody fragment being conjugated to a biotinyl enzyme capable of reacting with said biotinyl enzyme inhibitor;

(2) the ligand (1) to be measured; and (c) measuring the biotinyl enzyme inhibitory activity of said biologically active composition or the biotinyl enzyme activity of said aqueous solution.

5. The method of any one of claims 1–4, wherein said ligand (1) and said ligand (2) are selected from the group consisting of a hormone derived from an endocrine gland, a plasma protein, a viral antigen, bacteria, an α-fetoprotein, a carcinoembryonic antigen, a hapten or a first antibody in the double antibody method.

6. The method of any one of claims 1–4, wherein said ligand (1) and said ligand (2) are the same substance.

7. The method of any one of claims 1–4, wherein said antibody is produced from a warm-blooded animal.

8. The method of any one of claims 1–4, wherein said antibody is a monoclonal antibody.

9. The method of any one of claims 1–4, wherein said biotinyl enzyme is a member selected from the group consisting of a propionyl CoA carboxylase, acetyl CoA carboxylase, pyruvate carboxylase, methylmalonyl CoA carboxylase, methylmalonyl CoA transcarboxylase and methylcrotonyl CoA carboxylase.

10. The method of any one of claims 1–4, wherein said biotinyl enzyme inhibitor is avidin or streptoavidin.

11. The method of any one of claims 1–4, wherein the carrier material of said biologically active composition is a block-copolymer, graft-copolymer, two polymer materials which are attached to each other or two separate materials.

12. The method of any one of claims 1–4, wherein the measuring of the biotinyl enzyme activity is carried out by using a photon counter.

13. The method of any one of claims 1–4, wherein said aqueous solution is at a pH of about 5 to 8 and at a temperature of about 15° to 45° C.

14. The method of claim 13, wherein said aqueous solution is an aqueous buffer solution.

* * * * *